(12) United States Patent
Brotman et al.

(10) Patent No.: US 11,234,833 B2
(45) Date of Patent: Feb. 1, 2022

(54) EXPANDABLE LORDOSIS INTERVERTEBRAL IMPLANTS

(71) Applicant: NuVasive, Inc., San Diego, CA (US)

(72) Inventors: Michael Brotman, San Diego, CA (US); Sarah Stoltz, San Diego, CA (US); Jeremy Malik, San Diego, CA (US); Amanda Bloom, San Diego, CA (US); Brian Snider, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 268 days.

(21) Appl. No.: 15/738,098

(22) PCT Filed: May 12, 2016

(86) PCT No.: PCT/US2016/032216
§ 371 (c)(1),
(2) Date: Dec. 19, 2017

(87) PCT Pub. No.: WO2016/183382
PCT Pub. Date: Nov. 17, 2016

(65) Prior Publication Data
US 2018/0303621 A1    Oct. 25, 2018

Related U.S. Application Data

(60) Provisional application No. 62/190,251, filed on Jul. 9, 2015, provisional application No. 62/160,544, filed on May 12, 2015.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30331* (2013.01); *A61F 2002/30383* (2013.01); *A61F 2002/30405* (2013.01); *A61F 2002/30433* (2013.01); *A61F 2002/30471* (2013.01); *A61F 2002/30538* (2013.01); *A61F 2002/30624* (2013.01)

(58) Field of Classification Search
None
See application file for complete search history.

(56) References Cited

U.S. PATENT DOCUMENTS

| 5,171,278 | A  | 12/1992 | Pisharodi |
| 5,390,683 | A  | 2/1995  | Pisharodi |
| 5,693,100 | A  | 12/1997 | Pisharodi |
| 5,782,832 | A  | 7/1998  | Larsen et al. |
| 6,126,689 | A  | 10/2000 | Brett |
| 6,174,334 | B1 | 1/2001  | Suddaby |

(Continued)

FOREIGN PATENT DOCUMENTS

| AU | 2007202404 | 9/2016 |
| AU | 2011203582 | 9/2016 |

(Continued)

*Primary Examiner* — Sameh R Boles
(74) *Attorney, Agent, or Firm* — Hoffman Warnick LLC

(57) ABSTRACT

This present subject disclosure provides a novel implant which is readily adjustable to provide a precise angle of lordosis. The implant may be positioned while in low profile, collapsed geometry, and may be expanded when in place to provide a precise angle of lordosis.

13 Claims, 16 Drawing Sheets

(56) References Cited

U.S. PATENT DOCUMENTS

| | | |
|---|---|---|
| 6,183,517 B1 | 2/2001 | Suddaby |
| 6,332,895 B1 | 12/2001 | Suddaby |
| 6,340,369 B1 | 1/2002 | Ferree |
| 6,344,058 B1 | 2/2002 | Ferree |
| 6,352,557 B1 | 3/2002 | Ferree |
| 6,368,351 B1 | 4/2002 | Glenn |
| 6,409,766 B1 | 6/2002 | Brett |
| 6,419,702 B1 | 7/2002 | Ferree |
| 6,488,710 B2 | 12/2002 | Besselink |
| 6,491,724 B1 | 12/2002 | Ferree |
| 6,500,205 B1 | 12/2002 | Michelson |
| 6,582,451 B1 | 6/2003 | Marucci et al. |
| 6,648,918 B2 | 11/2003 | Ferree |
| 6,652,584 B2 | 11/2003 | Michelson |
| 6,709,458 B2 | 3/2004 | Michelson |
| 6,716,247 B2 | 4/2004 | Michelson |
| 6,719,797 B1 | 4/2004 | Ferree |
| 6,743,255 B2 | 6/2004 | Ferree |
| 6,793,679 B2 | 9/2004 | Michelson |
| 6,808,537 B2 | 10/2004 | Michelson |
| 6,814,756 B1 | 11/2004 | Michelson |
| 6,962,606 B2 | 11/2005 | Michelson |
| 6,972,035 B2 | 12/2005 | Michelson |
| 6,986,772 B2 | 1/2006 | Michelson |
| 7,008,453 B1 | 3/2006 | Michelson |
| 7,044,971 B2 | 5/2006 | Suddaby |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,118,579 B2 | 10/2006 | Michelson |
| 7,118,598 B2 | 10/2006 | Michelson |
| 7,547,325 B2 | 6/2009 | Biedermann et al. |
| 7,608,107 B2 | 10/2009 | Michelson |
| 7,615,052 B2 | 11/2009 | Serbousek |
| 7,621,951 B2 | 11/2009 | Glenn et al. |
| 7,625,377 B2 | 12/2009 | Veldhuizen et al. |
| 7,655,027 B2 | 2/2010 | Michelson |
| 7,678,148 B2 | 3/2010 | Peterman |
| 7,682,400 B2 | 3/2010 | Zwirkoski |
| 7,763,028 B2 | 7/2010 | Lim et al. |
| 7,763,074 B2 | 7/2010 | Altarac et al. |
| 7,846,206 B2 | 12/2010 | Oglaza et al. |
| 7,892,286 B2 | 2/2011 | Michelson |
| 7,901,409 B2 | 3/2011 | Canaveral et al. |
| 7,922,729 B2 | 4/2011 | Michelson |
| 8,007,534 B2 | 8/2011 | Michelson |
| 8,025,665 B2 | 9/2011 | Lim et al. |
| 8,075,621 B2 | 12/2011 | Michelson |
| 8,097,034 B2 | 1/2012 | Michelson |
| 8,097,035 B2 | 1/2012 | Glenn et al. |
| 8,128,662 B2 | 3/2012 | Altarac et al. |
| 8,152,837 B2 | 4/2012 | Altarac et al. |
| 8,182,538 B2 | 5/2012 | O'Neil et al. |
| 8,251,891 B2 | 8/2012 | Moskowitz et al. |
| 8,268,001 B2 | 9/2012 | Butler et al. |
| 8,303,658 B2 | 11/2012 | Peterman |
| 8,317,798 B2 | 11/2012 | Lim et al. |
| 8,328,818 B1 | 12/2012 | Seifert et al. |
| 8,377,071 B2 | 2/2013 | Lim et al. |
| 8,409,282 B2 | 4/2013 | Kim |
| 8,444,692 B2 | 5/2013 | Michelson |
| 8,496,664 B2 | 7/2013 | Michelson |
| 8,523,944 B2 | 9/2013 | Jimenez et al. |
| 8,540,452 B2 | 9/2013 | Jimenez et al. |
| 8,551,173 B2 | 10/2013 | Lechmann et al. |
| 8,579,907 B2 | 11/2013 | Lim et al. |
| 8,603,173 B2 | 12/2013 | Biedermann et al. |
| 8,628,577 B1 | 1/2014 | Jimenez |
| 8,663,329 B2 | 3/2014 | Ernst |
| 8,685,095 B2 | 4/2014 | Miller et al. |
| 8,690,917 B2 | 4/2014 | Suh et al. |
| 8,734,520 B2 | 5/2014 | Zwirkoski |
| 8,771,321 B2 | 7/2014 | Michelson |
| 8,771,358 B2 | 7/2014 | Michelson |
| 8,795,365 B2 | 8/2014 | Arcenio et al. |
| 8,795,374 B2 | 8/2014 | Chee |
| 8,828,085 B1 | 9/2014 | Jensen |
| 8,845,726 B2 | 9/2014 | Tebbe et al. |
| 8,845,730 B2 | 9/2014 | de Villiers et al. |
| 8,894,652 B2 | 11/2014 | Seifert et al. |
| 8,906,100 B2 | 12/2014 | Jimenez et al. |
| 8,940,049 B1 | 1/2015 | Jimenez et al. |
| 8,986,386 B2 | 3/2015 | Oglaza et al. |
| 8,998,992 B2 | 4/2015 | Seifert et al. |
| 9,005,291 B2 | 4/2015 | Loebl et al. |
| 9,034,040 B2 | 5/2015 | Seifert et al. |
| 9,039,742 B2 | 5/2015 | Altarac et al. |
| 9,119,726 B2 | 9/2015 | Wei |
| 9,125,692 B2 | 9/2015 | Kim |
| 9,138,327 B1 | 9/2015 | McClellan, III |
| 9,155,572 B2 | 10/2015 | Altarac et al. |
| 9,204,973 B2 | 12/2015 | Aflatoon et al. |
| 9,220,535 B2 | 12/2015 | Robling et al. |
| 9,259,328 B2 | 2/2016 | Pabst et al. |
| 9,289,308 B2 | 3/2016 | Marino et al. |
| 9,295,562 B2 | 3/2016 | Lechmann et al. |
| 9,333,093 B2 | 5/2016 | Aflatoon |
| 9,345,584 B2 | 5/2016 | Michelson |
| 9,351,846 B2 | 5/2016 | De Villiers et al. |
| 9,351,851 B2 | 5/2016 | Huffmaster et al. |
| 9,381,092 B2 | 7/2016 | Jimenez et al. |
| 9,393,130 B2 | 7/2016 | Suddaby et al. |
| 9,408,707 B2 | 8/2016 | Oglaza et al. |
| 9,408,721 B2 | 8/2016 | Eastlack et al. |
| 9,414,933 B2 | 8/2016 | Banouskou |
| 9,421,111 B2 | 8/2016 | Baynham |
| 9,433,510 B2 | 9/2016 | Lechmann et al. |
| 9,445,856 B2 | 9/2016 | Seifert et al. |
| 9,445,917 B2 | 9/2016 | Jimenez et al. |
| 9,463,099 B2 | 10/2016 | Levy et al. |
| 2003/0236520 A1 | 12/2003 | Lim et al. |
| 2005/0080422 A1 | 4/2005 | Otte et al. |
| 2005/0278036 A1 | 12/2005 | Leonard et al. |
| 2006/0004455 A1 | 1/2006 | Leonard et al. |
| 2007/0118222 A1 | 5/2007 | Lang |
| 2007/0149978 A1 | 6/2007 | Shezifi et al. |
| 2007/0282443 A1 | 12/2007 | Globerman et al. |
| 2008/0114367 A1 | 5/2008 | Meyer |
| 2009/0076607 A1 | 3/2009 | Aalsma et al. |
| 2009/0157084 A1 | 6/2009 | Aalsma et al. |
| 2009/0281628 A1 | 11/2009 | Oglaza et al. |
| 2010/0137862 A1 | 6/2010 | Diao et al. |
| 2010/0137987 A1 | 6/2010 | Diao et al. |
| 2010/0217335 A1 | 8/2010 | Chirico et al. |
| 2011/0029086 A1 | 2/2011 | Glazer et al. |
| 2011/0257748 A1 | 10/2011 | Liu |
| 2012/0101530 A1 | 4/2012 | Robling et al. |
| 2012/0290094 A1 | 11/2012 | Lim et al. |
| 2013/0103154 A1 | 4/2013 | Trieu et al. |
| 2013/0116791 A1 | 5/2013 | Theofilos |
| 2013/0144388 A1 | 6/2013 | Emery et al. |
| 2013/0158664 A1* | 6/2013 | Palmatier ............... A61F 2/447 623/17.16 |
| 2013/0190876 A1 | 7/2013 | Drochner et al. |
| 2013/0297029 A1 | 11/2013 | Kana et al. |
| 2013/0304213 A1 | 11/2013 | Aflatoon et al. |
| 2014/0018922 A1 | 1/2014 | Marino et al. |
| 2014/0031940 A1 | 1/2014 | Banouskou |
| 2014/0039625 A1 | 2/2014 | To et al. |
| 2014/0114420 A1 | 4/2014 | Robinson |
| 2014/0135776 A1 | 5/2014 | Huffmaster et al. |
| 2014/0148904 A1 | 5/2014 | Robinson |
| 2014/0156007 A1 | 6/2014 | Pabst et al. |
| 2014/0163682 A1 | 6/2014 | Lott et al. |
| 2014/0163683 A1 | 6/2014 | Seifert et al. |
| 2014/0180419 A1 | 6/2014 | Dmuschewsky |
| 2014/0236296 A1 | 8/2014 | Wagner et al. |
| 2014/0243983 A1 | 8/2014 | Galea et al. |
| 2014/0277139 A1 | 9/2014 | Vrionis et al. |
| 2014/0277492 A1 | 9/2014 | Wei |
| 2014/0277498 A1 | 9/2014 | Ainsworth et al. |
| 2014/0277499 A1 | 9/2014 | Ainsworth et al. |
| 2014/0277508 A1 | 9/2014 | Baynham |
| 2014/0296984 A1 | 10/2014 | Etminan |

(56) References Cited

U.S. PATENT DOCUMENTS

| | | |
|---|---|---|
| 2014/0309741 A1 | 10/2014 | Ganter et al. |
| 2014/0343677 A1 | 11/2014 | Davis et al. |
| 2014/0343678 A1 | 11/2014 | Suddaby et al. |
| 2014/0358246 A1 | 12/2014 | Levy et al. |
| 2014/0364951 A1 | 12/2014 | De Villiers et al. |
| 2015/0012098 A1 | 1/2015 | Eastlack et al. |
| 2015/0112437 A1 | 4/2015 | Davis et al. |
| 2015/0182347 A1 | 7/2015 | Robinson |
| 2015/0230935 A1 | 8/2015 | Aflatoon |
| 2015/0238230 A1 | 8/2015 | Suh et al. |
| 2015/0342586 A1 | 12/2015 | Lim et al. |
| 2016/0022434 A1 | 1/2016 | Robinson |
| 2016/0022438 A1 | 1/2016 | Lamborne et al. |
| 2016/0030190 A1 | 2/2016 | Robinson |
| 2016/0067056 A1 | 3/2016 | Armstrong et al. |
| 2016/0074174 A1 | 3/2016 | Halverson et al. |
| 2016/0081724 A1 | 3/2016 | Robling et al. |
| 2016/0089247 A1 | 3/2016 | Nichols et al. |
| 2016/0242927 A1 | 8/2016 | Seifert et al. |
| 2016/0250034 A1 | 9/2016 | Loebl et al. |
| 2016/0256148 A1 | 9/2016 | Huffmaster et al. |

FOREIGN PATENT DOCUMENTS

| | | |
|---|---|---|
| CN | 101502436 | 9/2016 |
| CN | 104248465 | 9/2016 |
| CN | 105232191 | 9/2016 |
| CN | 202568534 | 9/2016 |
| CN | 203183090 | 9/2016 |
| CN | 204306881 | 9/2016 |
| CN | 204931904 | 9/2016 |
| DE | 20314708 | 11/2003 |
| DE | 10344019 | 9/2016 |
| EP | 2777633 | 11/2003 |
| FR | 2717068 | 11/2003 |
| FR | 2813519 | 11/2003 |
| FR | 3006169 | 11/2003 |
| JP | 2008054710 | 11/2003 |
| JP | 2014073405 | 11/2003 |
| JP | 2016013460 | 11/2003 |
| KR | 100395252 | 11/2003 |
| KR | 20020084349 | 11/2003 |
| RU | 2070006 | 11/2003 |
| WO | WO200103616 | 11/2003 |
| WO | WO2005006944 | 11/2003 |
| WO | WO2006042334 | 11/2003 |
| WO | WO2007038349 | 11/2003 |
| WO | WO2007070024 | 11/2003 |
| WO | WO9214423 | 4/2008 |
| WO | WO9525485 | 4/2008 |
| WO | WO2008044057 | 4/2008 |
| WO | WO2010078468 | 4/2008 |
| WO | WO2012089317 | 4/2008 |
| WO | WO2014091028 | 4/2008 |
| WO | WO2014144696 | 4/2008 |
| WO | WO2014186384 | 4/2008 |
| WO | WO2015063719 | 4/2008 |
| WO | WO2015063721 | 4/2008 |
| WO | WO2015097416 | 4/2008 |
| WO | WO2015198335 | 4/2008 |
| WO | WO2016040125 | 4/2008 |

\* cited by examiner

EXPANDABLE LORDOSIS INTERVERTEBRAL IMPLANTS

This application claims priority to U.S. Provisional Patent Application Ser. No. 62/190,251, filed on Jul. 9, 2015; and to U.S. Provisional Patent Application Ser. No. 62/160,544, filed on May 12, 2015; the contents of which are hereby incorporated by reference herein in their entirety into this disclosure.

TECHNICAL FIELD

The subject disclosure relates generally to spinal implants. Specifically, the subject disclosure relates to expandable lordosis intervertebral implants.

BACKGROUND OF THE SUBJECT DISCLOSURE

Back problems are one of the most common and debilitating occurrences in people of all ethnicities. In the United States alone, over 500,000 spine lumbar and cervical fusion procedures are performed each year. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF) and lateral lumbar interbody fusion procedures are two of the techniques that spine surgeons use to access the portions of the spine to be repaired or replaced. Replacement of injured or deteriorated spinal bone with artificial implants requires a balance of knowledge of the mechanisms of the stresses inherent in the spine, as well as the biological properties of the body in response to the devices. Further, the size, configuration, and placement of an artificial implant requires precision positioning and handling by a skilled surgeon.

SUMMARY OF THE SUBJECT DISCLOSURE

The present subject disclosure provides a novel implant device which may be adjusted to form a particular lordosis angle depending on the needs or the functionality of the particular placement of the implant.

In one exemplary embodiment, the subject matter is an implant device. The device includes a first substantially planar plate; a second substantially planar plate; a linkage between the first and second plates; wherein a translation mechanism in the second plate causes the linkage to move from a collapsed position wherein the first plate and the second plate are substantially parallel with each other to an expanded position wherein the first plate is pushed away from the second plate such that the first plate and the second plate form an angle with respect to each other.

In another exemplary embodiment, the subject matter is an implant device. The device includes a top plate having an extended anterior wall; a bottom plate having an extended anterior wall; a linkage between the top and bottom plates; wherein a translation mechanism in the bottom plate causes the linkage to move from a collapsed position wherein the extended anterior wall of the top plate and the extended anterior wall of the bottom plate are substantially parallel with each other to an expanded position wherein the top plate is pushed away from the bottom plate in a direction such that the extended anterior wall of the top plate and the extended anterior wall of the bottom plate form an angle with respect to each other.

In yet another exemplary embodiment, the subject matter is a method of inserting an adjustable lordosis intervertebral implant. The method includes accessing a disc space via a lateral approach; inserting the implant into the prepared disc space in its collapsed position having zero degrees of lordosis; rotating a threaded coupling in the implant using an expansion tool, thereby causing a drive shaft to translate in a proximal direction; expanding the implant until a desired degree of lordosis is achieved; withdrawing the expansion tool from the implant; attaching a fixation tab to the proximal end of the implant; and inserting a screw through the fixation tab into the vertebral body.

BRIEF DESCRIPTION OF THE DRAWINGS

Many advantages of the present subject disclosure will be apparent to those skilled in the art with a reading of this specification in conjunction with the attached drawings, which include.

DETAILED DESCRIPTION OF THE SUBJECT DISCLOSURE

Figure 1:
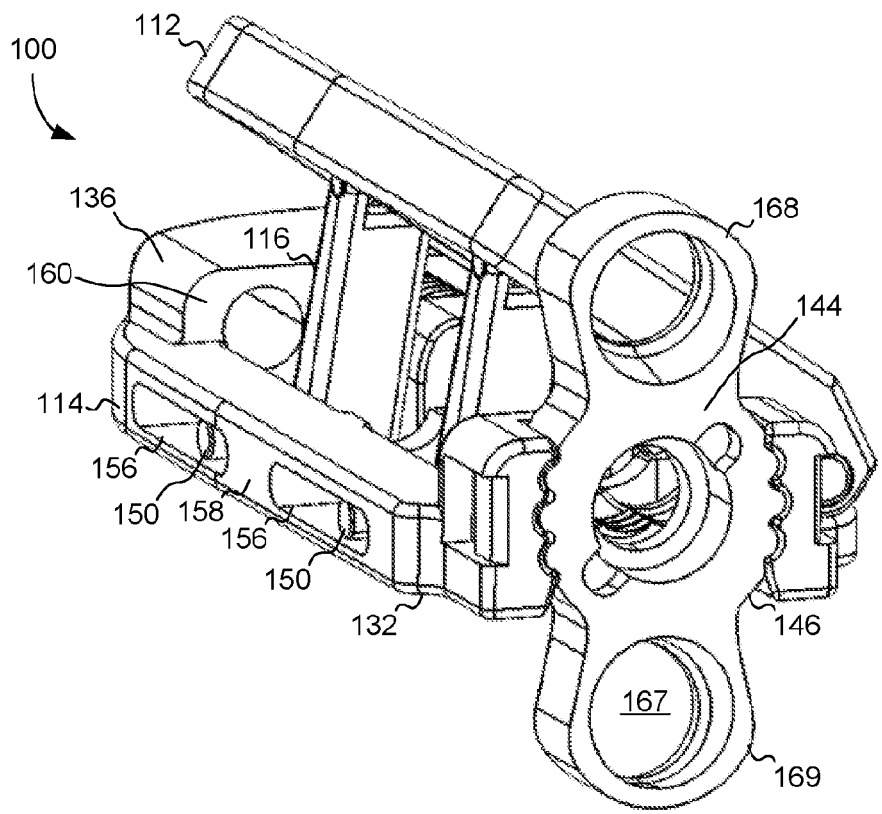
FIG. 1 shows a top perspective view of an expanded implant, according to a first exemplary embodiment of the subject disclosure.
Figure 2:
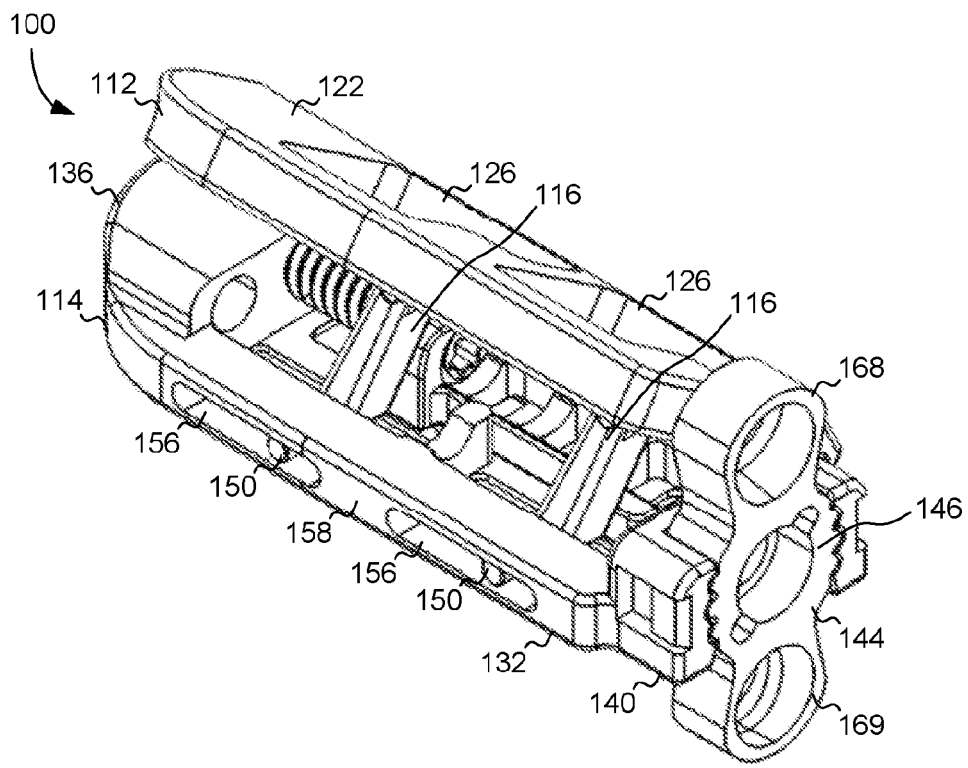
FIG. 2 shows another top perspective view of an expanded implant, according to a first exemplary embodiment of the subject disclosure.

The following detailed description references specific embodiments of the subject disclosure and accompanying figures, including the respective best modes for carrying out each embodiment. It shall be understood that these illustrations are by way of example and not by way of limitation.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The adjustable lordosis implant and related methods disclosed herein boast a variety of novel features and components that warrant patent protection, both individually and in combination.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The subject disclosure relates to an expandable lordosis intervertebral implant. The implant has a collapsed configuration and an expanded configuration, and is designed to be placed into an intervertebral disc space in its collapsed configuration and then expanded while in the disc space to its expanded configuration. When the implant is in its expanded configuration, it creates a lordotic angle in the disc space (i.e., the anterior height of the implant is greater than the posterior height of the implant). The exemplary embodiments of the implant as shown and described herein are dimensioned for use in a direct lateral approach to the spine, however, it is contemplated that a similar implant with a similar expansion mechanism could be used in an anterior approach to the spine.

As shown in FIGS. 1-8, the first exemplary embodiment of the implant 100 comprises a top plate 112, a bottom plate 114, linkages 116 connecting the top and bottom plates 112, 114, a drive shaft 118 (see FIG. 8) coupled to the linkages 116 and a threaded coupling 120 between the bottom plate 114 and the drive shaft 118.

Figure 3:
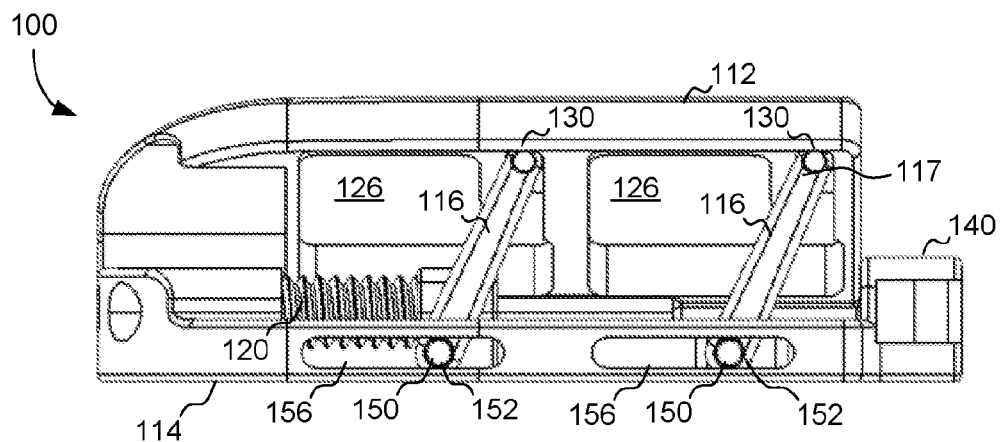
FIG. 3 shows a front view of an expanded implant, according to a first exemplary embodiment of the subject disclosure.
Figure 4:
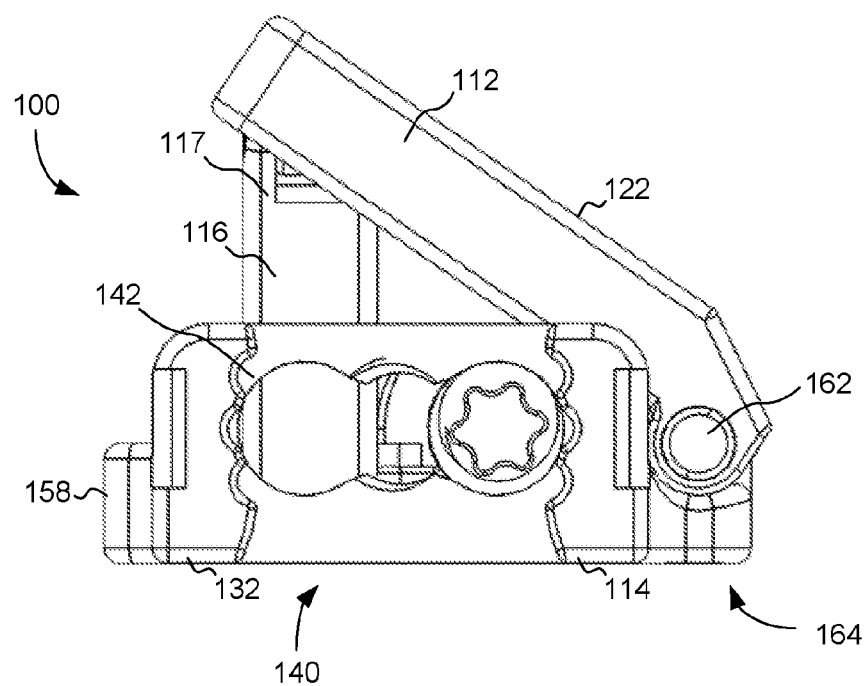
FIG. 4 shows a proximal side view of an expanded implant, according to a first exemplary embodiment of the subject disclosure.
Figure 5:
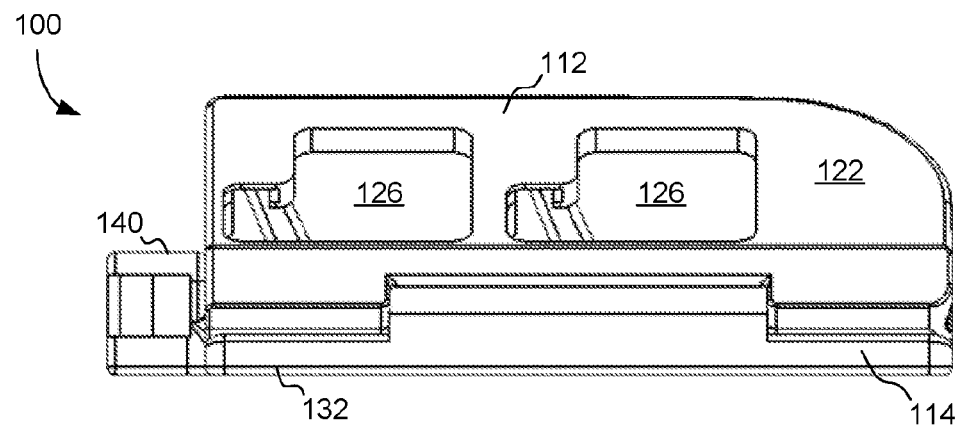
FIG. 5 shows a back view of an expanded implant, according to a first exemplary embodiment of the subject disclosure.
Figure 6:
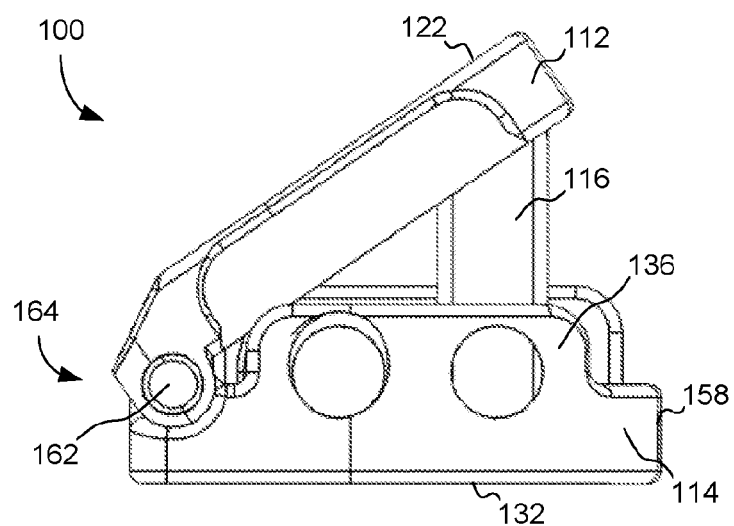
FIG. 6 shows a distal side view of an expanded implant, according to a first exemplary embodiment of the subject disclosure.
Figure 7:
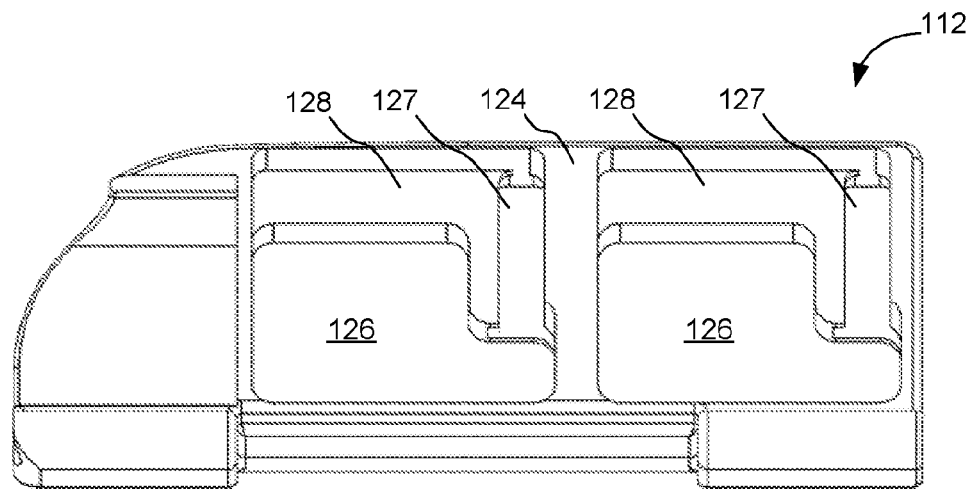
FIG. 7 shows a bottom view of a top plate of an implant, according to a first exemplary embodiment of the subject disclosure.
Figure 8:
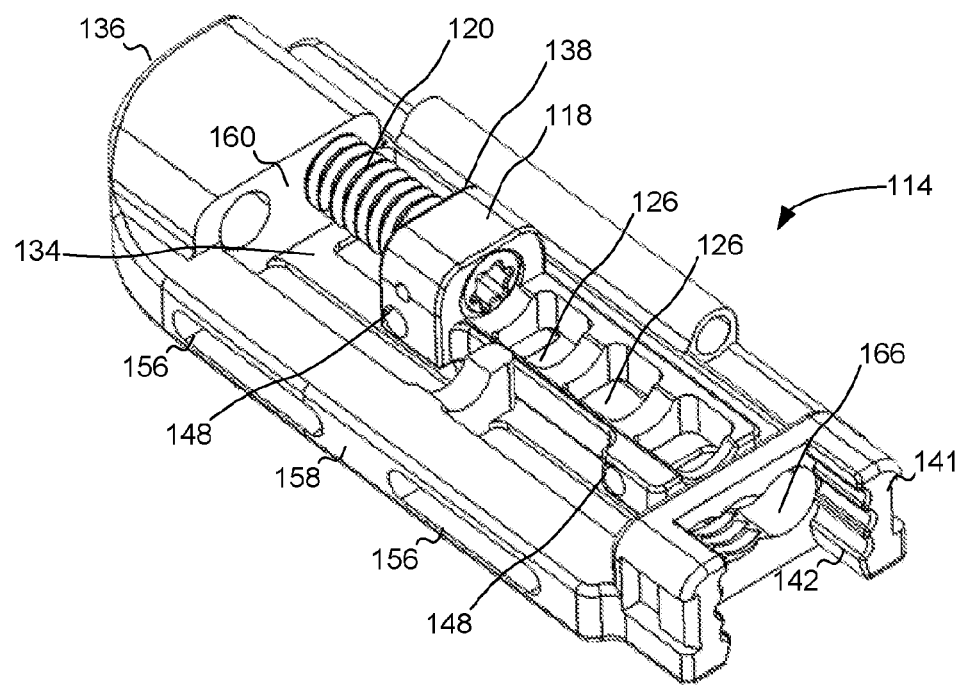
FIG. 8 shows a perspective view of a bottom plate of an implant, according to a first exemplary embodiment of the subject disclosure.

The top plate 112 has an upper bone contacting surface 122 and an opposite interior surface 124 (see FIG. 7). As shown in the exemplary embodiment, the top plate 112 includes one or more fusion apertures 126 extending through the bone contacting surface 122 and interior surface 124. The interior surface 124 includes recesses 128 to accommodate the linkages 116 in the interior of the implant 100. The recesses 128 further comprise a pocket 127 that houses the superior ends 117 of the linkages 116. As shown in FIG. 3, the superior ends 117 of the linkages 116 are coupled to the interior surface 124 of the top plate 112 via a pivot pin 130.

The bottom plate 114 has a lower bone contacting surface 132 and an opposite interior surface 134. The bottom plate 114 includes one or more fusion apertures 126 extending through the lower bone contacting surface 132 and the opposite interior surface 134. The distal wall 136 of the lower plate 114 includes a threaded hole for receiving the threaded coupling 120. The anterior wall 140 of the bottom plate 114 includes pin slots (not shown) configured to receive pins that couple the inferior end of the linkages 116 to the bottom plate 114. The proximal end 141 of the bottom plate 114 includes a recess 142 configured to receive a detachable fixation tab 144. The recess 142 has a shape that complements the shape of the attachment portion 146 of the detachable fixation tab 144. As shown in the exemplary embodiment, the recess 142 and the attachment portion 146 of the detachable tab 144 are generally flower shaped to allow the tab 144 to be attached in a variety of positions, however, other shapes may be implemented.

The interior surface 134 of the bottom plate 114 houses the drive shaft 118. As illustrated in the exemplary embodiment in FIGS. 1-8, the interior surface 134 of the bottom plate 114 includes a track dimensioned to receive the drive shaft 118. As shown best in FIGS. 3 and 8, the distal end 138 of the drive shaft 118 includes a hole for receiving the threaded coupling 120. The drive shaft 118 further includes pin holes 148 dimensioned to receive the pin 150 that couples the inferior end 152 of the linkages 116 to the bottom plate 114. One end of the pin 150 resides and translates within the slots 156 in the anterior wall 158 of the bottom plate 114, the center of the pin 150 is received in a pin hole through the inferior end 152 of the linkages 116 and a second end of the pin 150 is received in the pin hole 148 in the drive shaft 118.

The drive shaft 118 is configured such that when the implant 100 is in its collapsed configuration, the distal surface 138 of the drive shaft 118 is in close proximity to the proximal face 160 of the distal wall 136 of the bottom plate 114. As the threaded coupling 120 is rotated in a first direction, the drive shaft 118 translates in a proximal direction. Translation of the drive shaft 118 in the proximal direction causes the pins 150 received through the inferior ends 152 of the linkages 116 to slide proximally within the pin slots 156 in the bottom plate 114 while causing the linkages 116 to pivot about the pivot pin 130 coupled to the top plate 112. The pivoting of the linkages 116 about the pivot pin 130 allows the linkages 116 to move from a first, generally horizontal position in the interior of the implant 100 to a second, more vertical position, pushing the top plate 112 upwards and thereby causing a change in the anterior height of the implant 100 when the implant is in its expanded state. The top plate 112 is coupled to the bottom plate 114 via a hinge 162 on the posterior side 164 of the implant 100. The described expansion mechanism allows the lordotic angle of the implant 100 to be increased in non-discrete increments, meaning the surgeon can increase the angle of lordosis until the desired amount of lordosis is reached.

Figure 31:
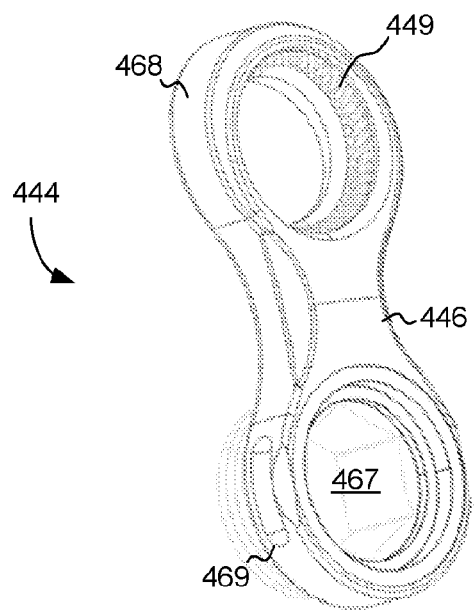
FIG. 31 shows a perspective view of a fixation device with an anti-backout device, according to an exemplary embodiment of the subject disclosure.
Figure 32:
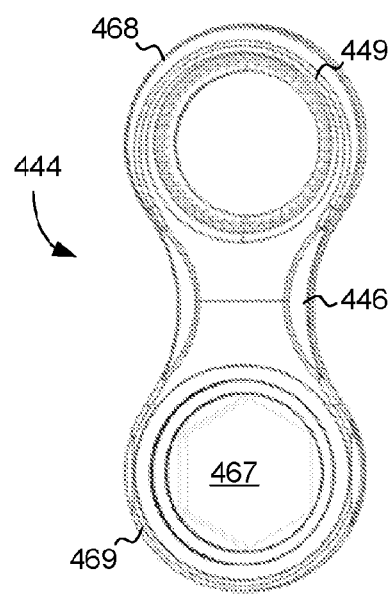
FIG. 32 shows a top view of a fixation device with an anti-backout device, according to an exemplary embodiment of the subject disclosure.
Figure 33:
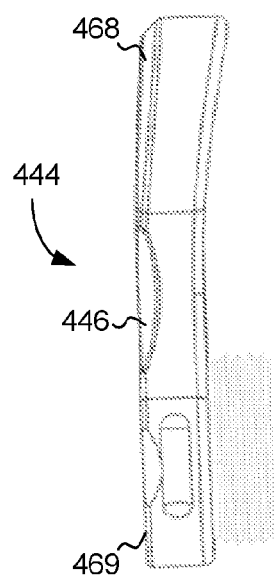
FIG. 33 shows a side view of a fixation device with an anti-backout device, according to an exemplary embodiment of the subject disclosure.

Once the implant 100 has been expanded to the desired level of lordosis, the implant 100 can be packed with bone graft or bone graft substitute through the same hole 166 through which instruments used to actuate the drive mechanism are inserted. Upon packing the implant 100 with bone graft or bone graft substitute, the fixation tab 144 is coupled to the proximal end 141 of the implant 100. As shown in the exemplary embodiment, the fixation tab 144 includes a superior and an inferior extension 168, 169 with a screw hole 167 therethough. The superior extension 168 is configured to be positioned adjacent the superior vertebral body and the inferior extension 169 is configured to be positioned adjacent the inferior vertebral body. A fixation tab 144 with a single extension for receiving a single screw therethrough and positioned adjacent only one of the superior and inferior vertebral body is also contemplated. It is also contemplated that the extensions include an anti-backout element for preventing backout of the screws after they've been placed through the extension and into the vertebral body. Further details of an exemplary fixation tab 144 are shown in FIGS. 31-33.

According to the exemplary embodiment shown in FIGS. 1-8, a method of using the implant 100 is as follows: a disc space is accessed via a lateral approach; the disc space is prepared to receive an intervertebral implant; the implant 100 is inserted into the prepared disc space in its collapsed position having 0 degrees of lordosis; an expansion tool is used to rotate the threaded coupling 120, thereby causing the drive shaft 118 to translate in a proximal direction; the implant 100 is expanded until the desired degree of lordosis is achieved; the expansion tool is withdrawn from the implant 100; bone graft or bone graft substitute is packed into the interior of the implant 100; a fixation tab 144 is attached to the proximal end 140 of the implant 100 and at least one screw is inserted through the fixation tab 144 into the vertebral body.

FIGS. 9-14 illustrate an alternative embodiment of the expandable lordosis intervertebral implant. The implant according to this embodiment shares many of the same features as the implant of FIGS. 1-8. The same features and elements will not be re-described in this embodiment but may be labeled using a "2" instead of a "1" as the first digit of the three digit label. The reader should understand that the features are the same or similar as in the first embodiment. Attention will be directed to the distinctions between this embodiment and the embodiment presented in FIGS. 1-8. One of the differences according to this alternative embodiment is that the top plate 212 and the bottom plate 214 include planar extensions 213, 215 that together define an anterior wall when the implant 200 is in its expanded state. These planar extensions 213, 215 are configured to enclose the generally hollow interior of the implant 200.

Figure 9:
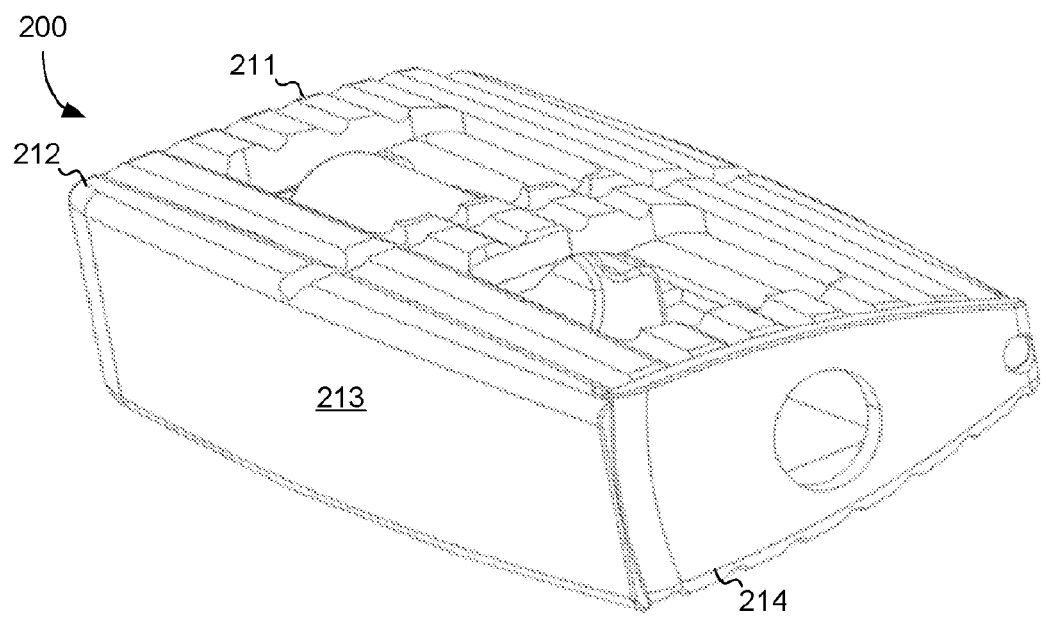
FIG. 9 shows a top perspective view of a collapsed implant, according to a second exemplary embodiment of the subject disclosure.
Figure 10:
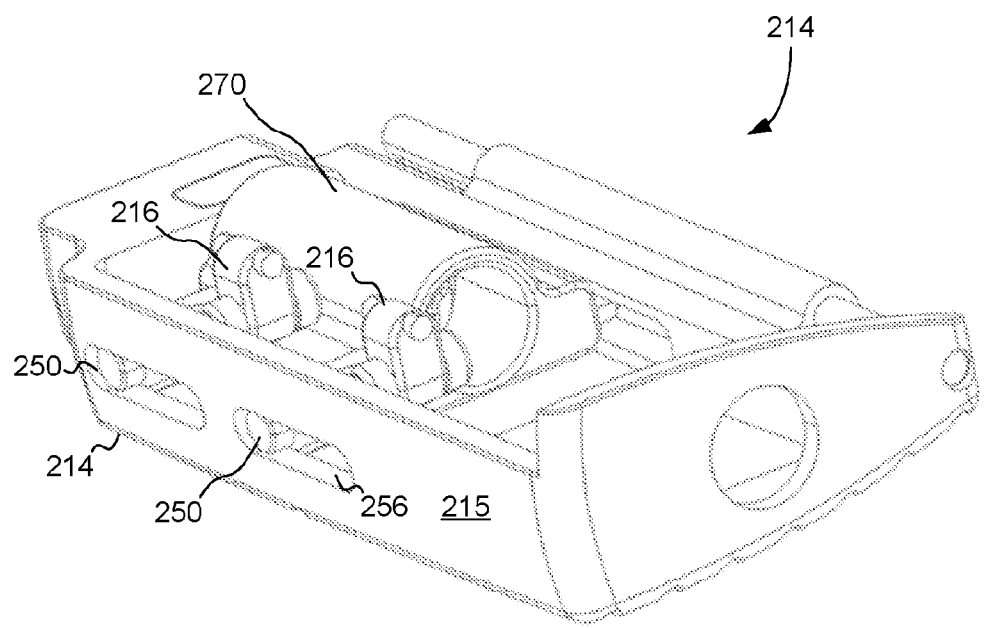
FIG. 10 shows a top perspective view of only the bottom plate of a collapsed implant, according to a second exemplary embodiment of the subject disclosure.
Figure 11:
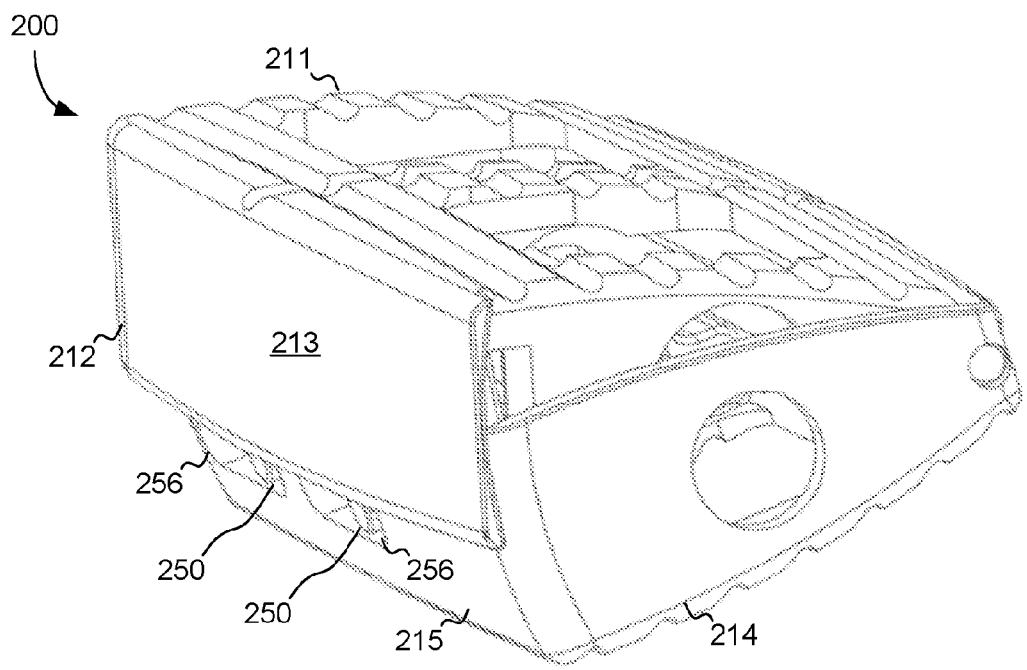
FIG. 11 shows a top perspective view of an expanded implant, according to a second exemplary embodiment of the subject disclosure.
Figure 12:
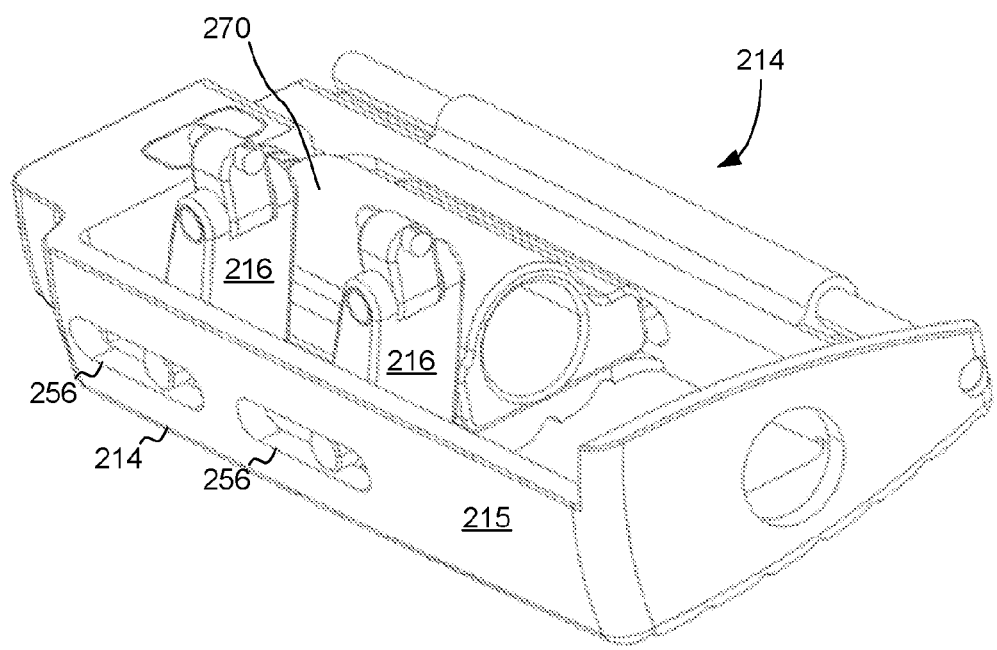
FIG. 12 shows a top perspective view of only the bottom bottom plate of an expanded implant, according to a second exemplary embodiment of the subject disclosure.
Figure 13:
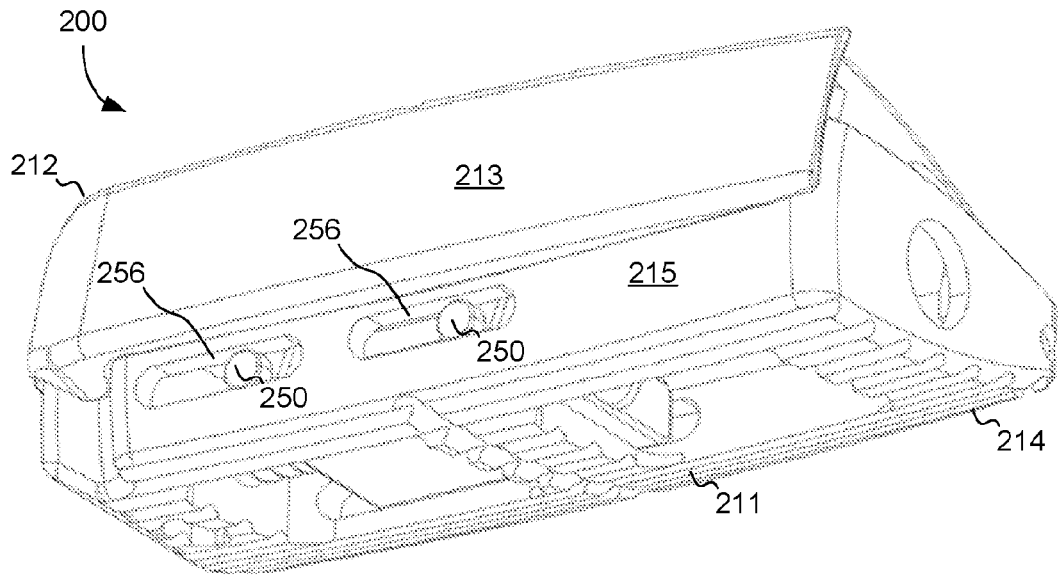
FIG. 13 shows a bottom perspective view of an expanded implant, according to a second exemplary embodiment of the subject disclosure.
Figure 14:
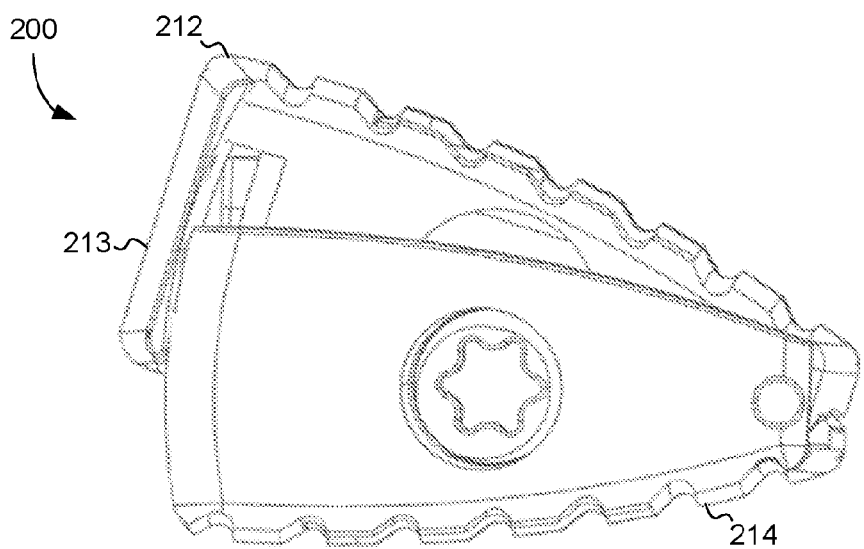
FIG. 14 shows a proximal side view of an expanded implant, according to a second exemplary embodiment of the subject disclosure.
Figure 15:
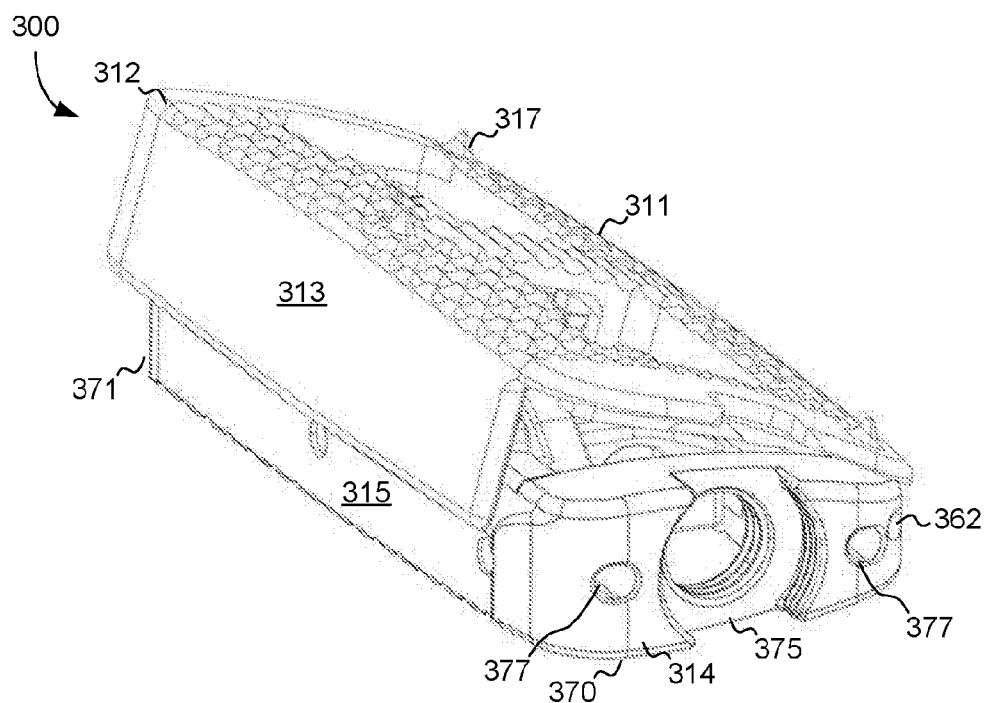
FIG. 15 shows a top perspective view of an expanded implant, according to a third exemplary embodiment of the subject disclosure.
Figure 16:
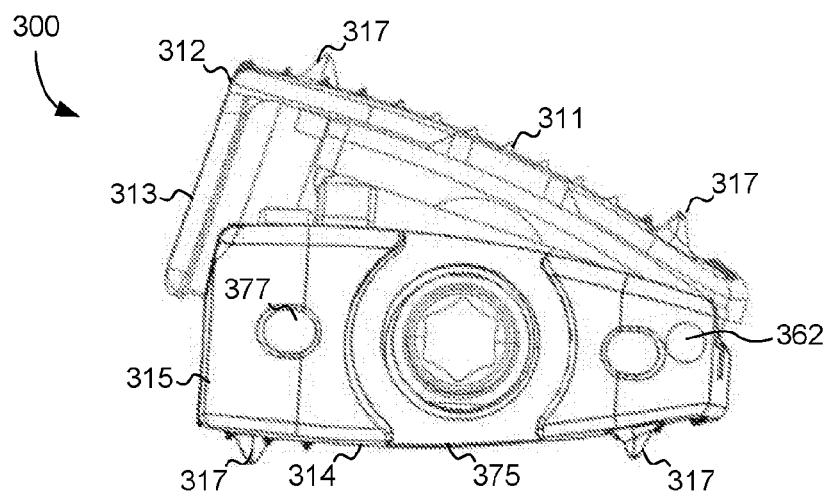
FIG. 16 shows a proximal side view of an expanded implant, according to a third exemplary embodiment of the subject disclosure.
Figure 17:
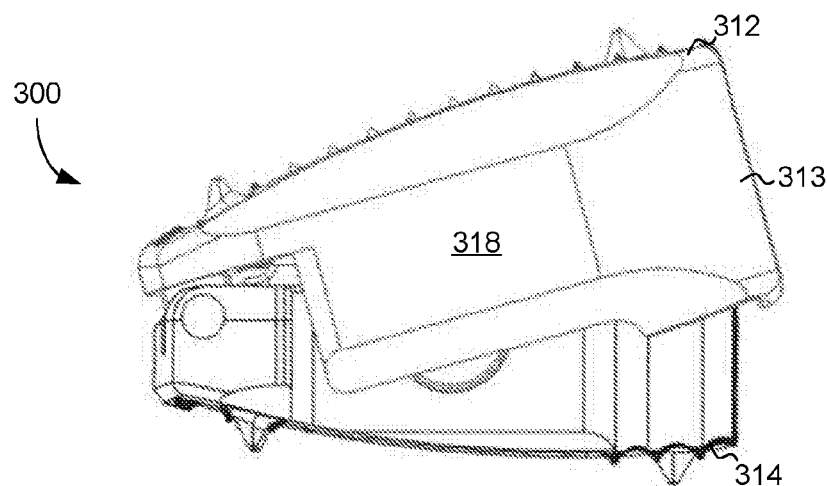
FIG. 17 shows a distal side view of an expanded implant, according to a third exemplary embodiment of the subject disclosure.
Figure 18:
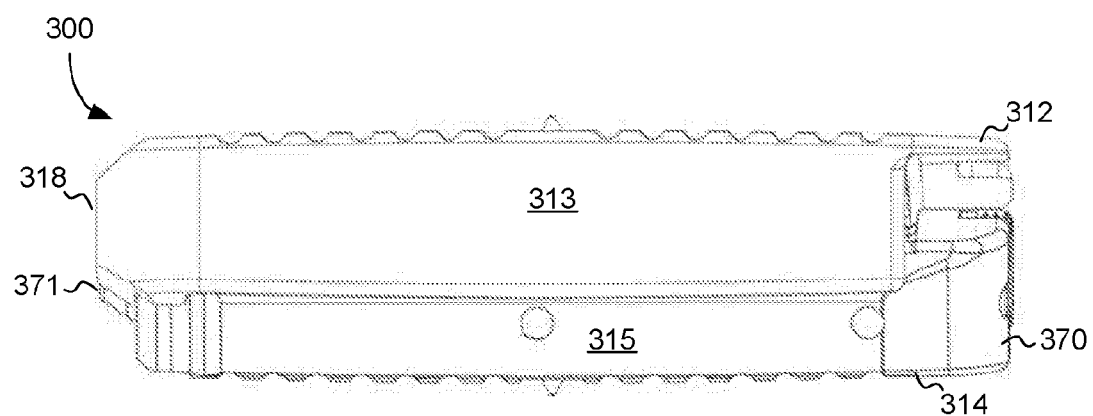
FIG. 18 shows a back view of an expanded implant, according to a third exemplary embodiment of the subject disclosure.
Figure 19:
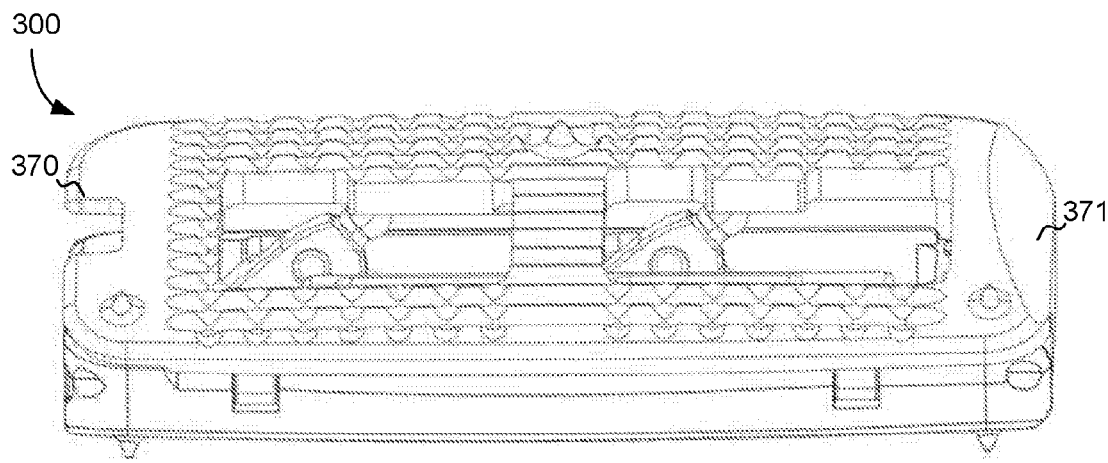
FIG. 19 shows a back perspective view of a collapsed implant, according to a third exemplary embodiment of the subject disclosure.
Figure 20:
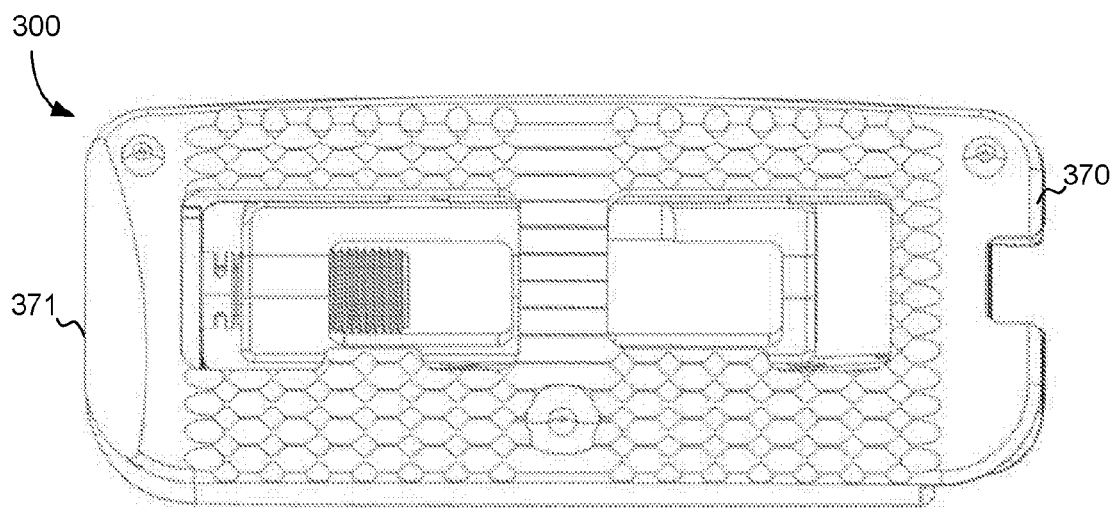
FIG. 20 shows a top view of a collapsed implant, according to a third exemplary embodiment of the subject disclosure.
Figure 21:
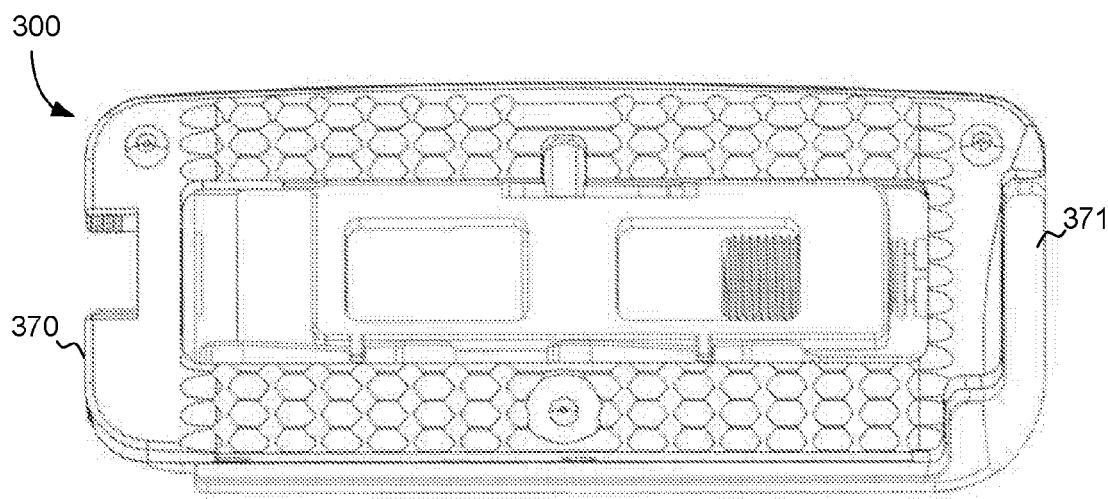
FIG. 21 shows a bottom view of a collapsed implant, according to a second exemplary embodiment of the subject disclosure.

The expansion mechanism of the device 200 according to the alternative embodiment of FIGS. 9-14 include a chassis 270 with a threaded interior. The drive screw 390 resides within the chassis 270 and has threads that engage the threaded interior of the chassis 270. Turning the drive screw causes the chassis 270 to translate proximally, consequently causing pins 250 coupled to the chassis 270 to translate proximally within slots 256 in the bottom anterior wall 215 of the bottom plate 214. Linkages 216 are coupled to these pins 250 at their inferior end and coupled to the top plate 212, such that when the chassis 270 translates proximally, the inferior ends of the linkages 216 are moved proximally, causing the linkages 216 to move to a more upright position and thereby causing the top plate 212 to move upward and away from the bottom plate 214, increasing the height and lordotic angle of the implant. This motion may be viewed in the figures as FIGS. 9 and 10 show the implant 200 in a low profile, closed/collapsed configuration. FIG. 10 shows the position of the various components with the top plate 212 removed for a better depiction of the mechanism, with pins 250 in a distal most position within their respective slots 256. FIGS. 11 and 12 show the implant 200 in an open, expanded, lordotic angle configuration. FIG. 12 shows the position of the various components with the top plate 212 removed for a better depiction of the mechanism, with pins 250 having been translated proximally within slots 256, thereby pushing linkages 216 in a vertical manner, which results in the lifting of the top plate 212. FIGS. 13 and 14 show the implant 200 from a lower perspective view (FIG. 13) and a side view (FIG. 14) in an open, expanded position with pins 250 having been translated proximally within slots 256, thereby pushing linkages 216 in a vertical manner, which results in the lifting of the top plate 212

The alternative embodiment presented in FIGS. 9-14 presents alternative additional features not shown in FIGS. 1-8. The top plate 212 has an additional top anterior cover 213 and the bottom plate 214 has an additional bottom anterior cover 215 which together serve to cover the entire anterior portion of the implant 200 when in a collapsed or expanded implant configuration. Further, top anterior cover 213 is lifted along with the top plate 212 when the pins 250 are slid proximally within the pin slots 256. Anti-migration features 211 on the exterior portions of both the top plate 212 and the bottom plate 214 serve to provide further frictional and contact surface between the implant 200 and the adjoining vertebrae.

Though not shown, it is contemplated that the second embodiment presented in FIGS. 9-14 would also have an attachment feature for receiving a fixation tab 144 as previously described in the first embodiment presented in FIGS. 1-8. The method of use of the second embodiment would also be the same as the method of use described for the first embodiment.

FIGS. 15-30 illustrate a further alternative embodiment of the expandable lordosis intervertebral implant. The implant according to this embodiment shares many of the same features as the exemplary embodiment of FIGS. 1-8, and the exemplary embodiment of FIGS. 9-14. The same features will not be re-described in this embodiment but may be labeled using a "3" instead of a "1" or "2" as the first digit of the three digit label. The reader should understand that the features are the same or similar as in the first and second embodiments. Attention will be directed to the distinctions between this embodiment and the prior described embodiments. Similar to the embodiment shown and described in FIGS. 9-14, the present embodiment also has a top plate 312 and a bottom plate 314 which include planar extensions 313, 315 that together define an anterior wall when the implant 300 is in its expanded state. These extensions 313, 315 are configured to enclose the generally hollow interior of the implant 300. An additional feature is a number of projections 317 on both the top plate 312 external surface and bottom plate 314 external surface. These fang-like projections 317 work in conjunction with the anti-migration features 311 on the top plate 312 and bottom plate 314 surfaces to create a friction fit with adjoining vertebrae.

The top plate 312 has a top anterior wall 313 with a further side wall 318 located at the distal end 371 of the implant 300, away from the insertion port 375 located at the proximal end 370 of the implant 300. This contra-lateral and anterior design has an opening and closing mechanism similar to that described in FIGS. 9-14 and akin to standard garage doors. Additional apertures 377 may be used in conjunction with insertion port 375 as receiving apertures for an oblong inserter tool (not shown). Pin 362 is used to connect the top plate 312 with the bottom plate 314, and serves as an axis of rotation of one plate with respect to the other.

Figure 22:
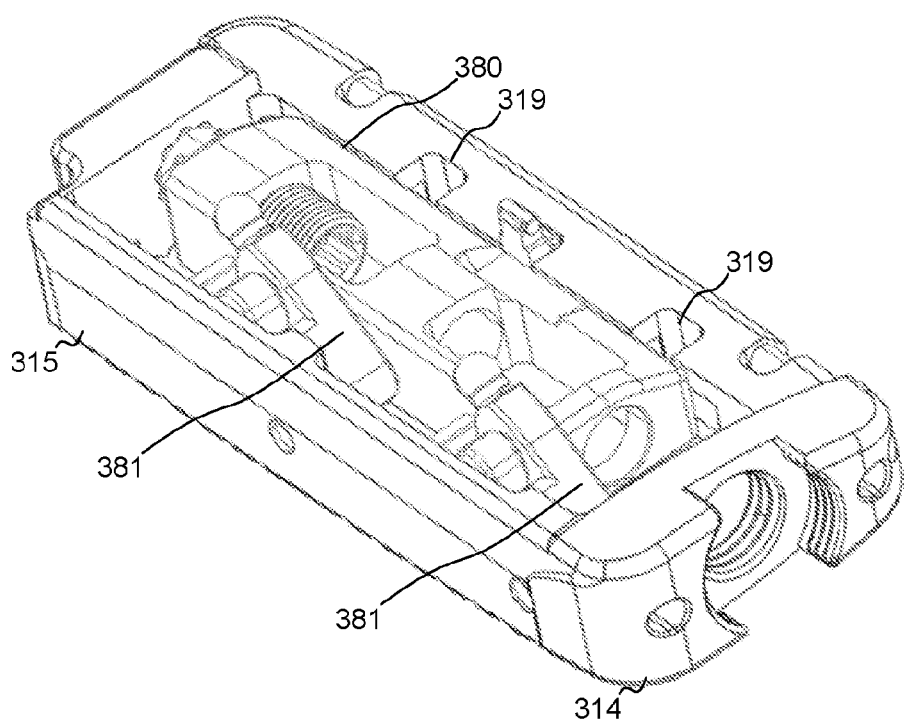
FIG. 22 shows a top perspective view of a bottom plate of an implant including a chassis, according to a third exemplary embodiment of the subject disclosure.
Figure 23:
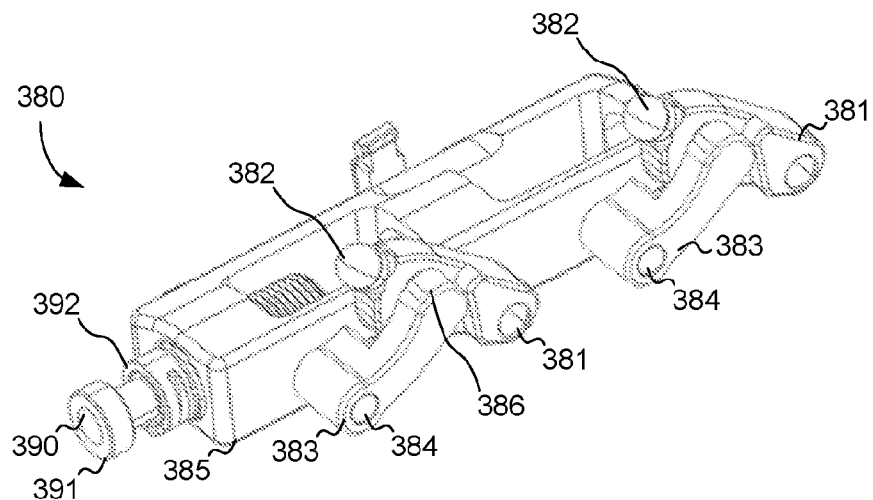
FIG. 23 shows a front perspective view of a chassis of an implant, according to a third exemplary embodiment of the subject disclosure.
Figure 24:
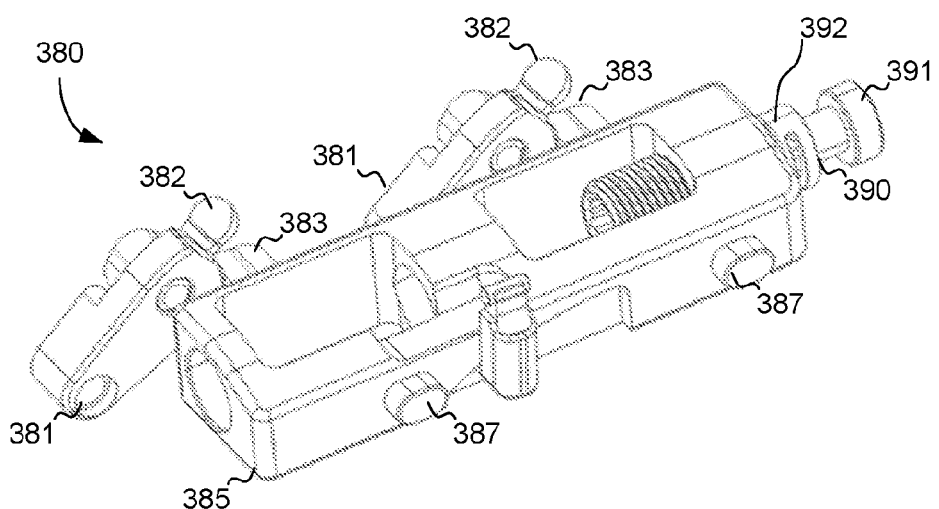
FIG. 24 shows a back perspective view of a chassis of an implant, according to a third exemplary embodiment of the subject disclosure.
Figure 25:
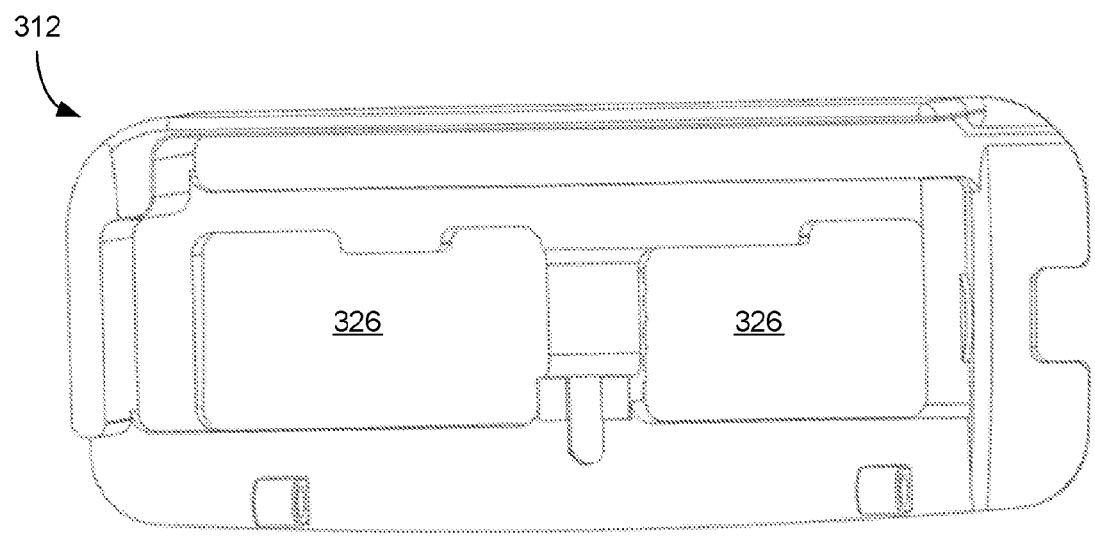
FIG. 25 shows a bottom view of a top plate of an implant, according to a second exemplary embodiment of the subject disclosure.
Figure 26:
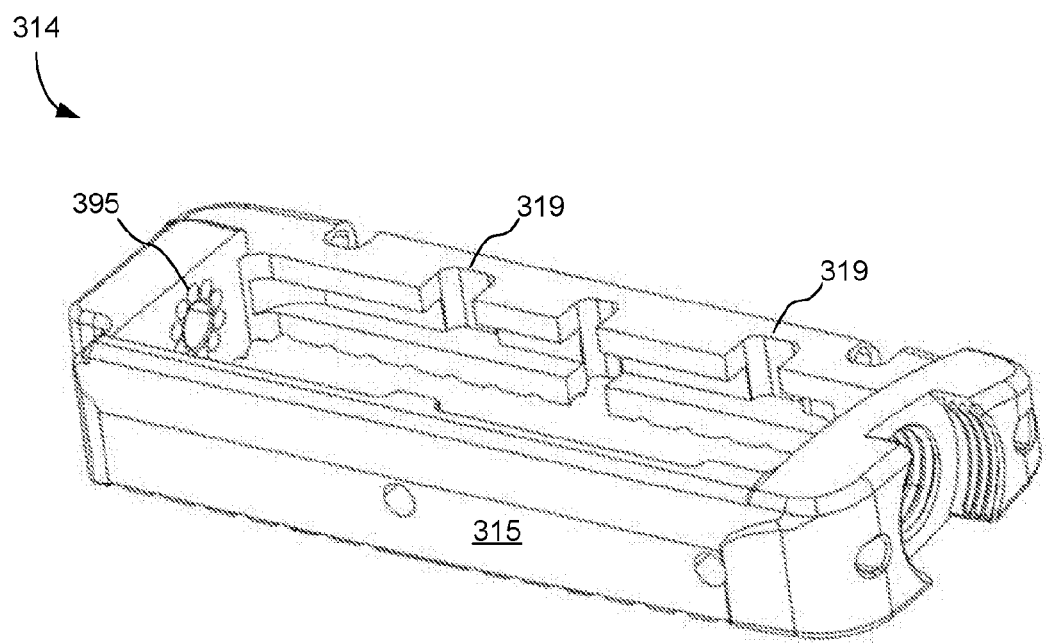
FIG. 26 shows a front perspective view of a bottom plate of an implant with chassis removed, according to a third exemplary embodiment of the subject disclosure.
Figure 27:
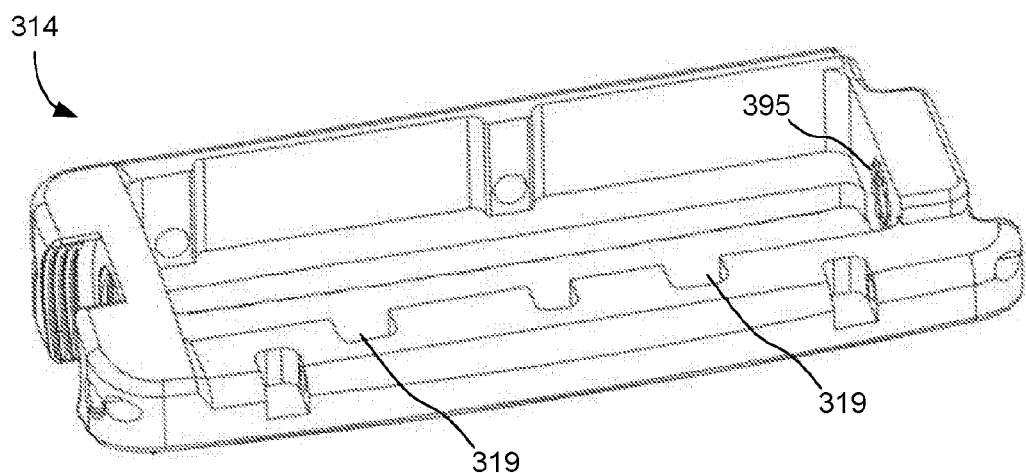
FIG. 27 shows a back perspective view of a bottom plate of an implant with chassis removed, according to a third exemplary embodiment of the subject disclosure.
Figure 28:
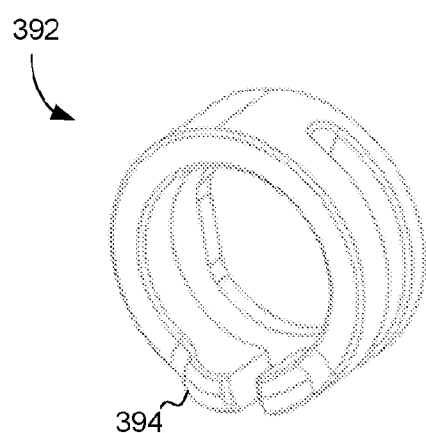
FIG. 28 shows a perspective view of a raptor spring, according to a third exemplary embodiment of the subject disclosure.

FIGS. 22-24 show a chassis 380 and its relative positioning within the bottom plate 314. A set of primary linkages 381 having spherical end portions 382 are connected to a set of support linkages 383, which are connected to the body portion 385 of the chassis 380 via pins 384. The pins 384 serve as the axis of rotation of the support linkages 383, which in turn allow for rotation of the primary linkages 381 via pins 386. The primary linkages 381 are not directly connected to the chassis body 385. Thus, the primary linkages 381 only articulate about a rotational axis formed by pins 386, and do not translate. The support linkages 383 both articulate and translate.

Chassis 380 includes oval protrusions 387 which are aligned with channels 319 and used to "drop down" the chassis 380 within the internal frame of the bottom plate 314 and then shift the chassis 380 back distally to lock the chassis 380 within the frame of the bottom plate 314. This mechanism secures the position of the chassis 380 with respect to the bottom plate 314.

Figure 29:
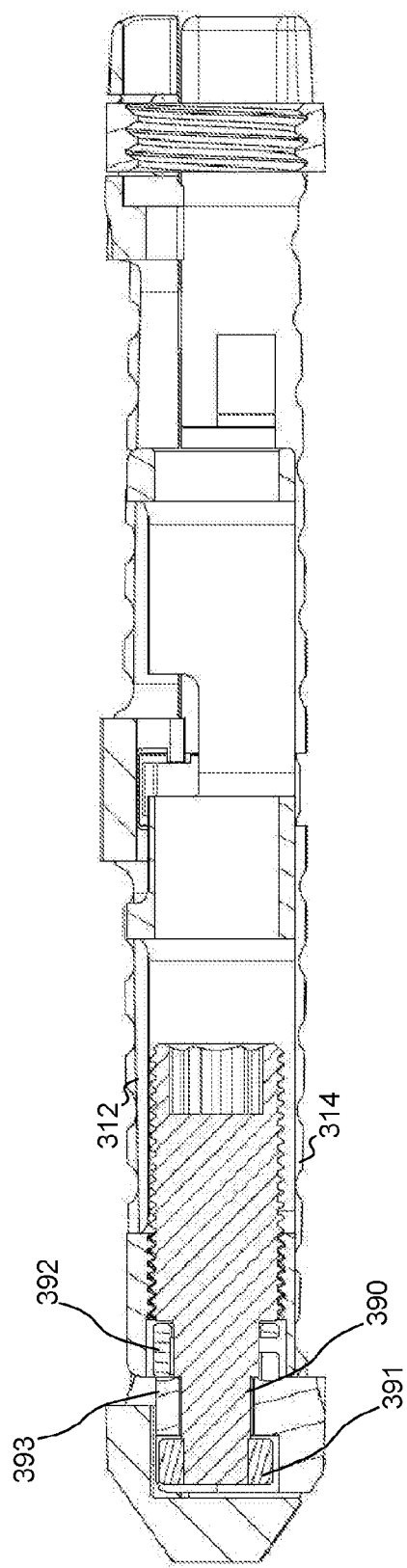
FIG. 29 shows a planar cut section of an implant, according to a third exemplary embodiment of the subject disclosure.

Screw 390 in conjunction with washer 391 act to lock the expansion/collapsing mechanism within chassis 380. As shown in FIG. 29, the screw 390 with washer 391 are locked into position by a friction fit within an accommodating portion 393 of the bottom plate 314. Additionally, raptor spring 392 has a protrusion 394 which provides further a locking mechanism for the screw 390 to position it within place. The protrusion 394 mates with divots 395 positioned annularly to form an annular flower pattern. A divot is available every 15-20 degrees such that a ratcheting mechanism is available for the surgeon to determine the precise level of openness of the top plate 312 is desired. Once such a lordosis angle is determined, the protrusion 394 of the spring 392 is allowed to mate with divot 395 of the bottom plate 314, to essentially lock the position and prevent further movement. Some level of force is required to further open or close the top plate 312.

Figure 30:
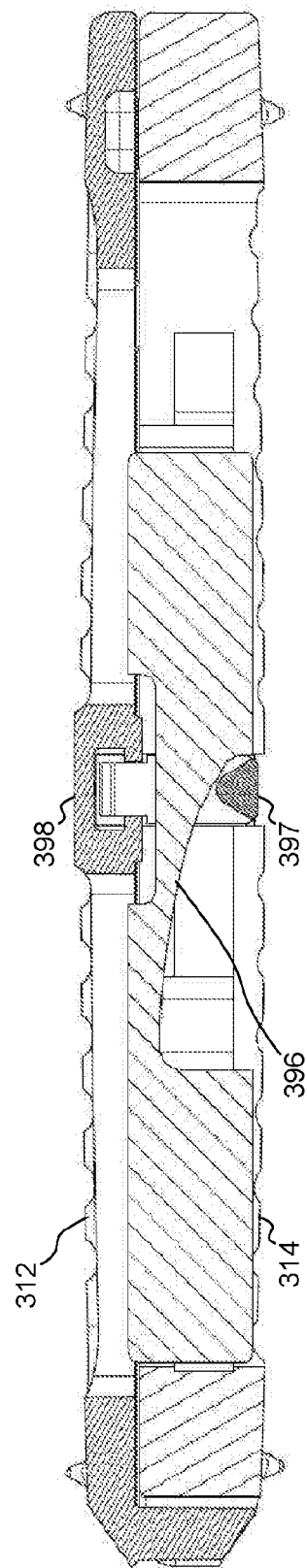
FIG. 30 shows another planar cut section of an implant, according to a third exemplary embodiment of the subject disclosure.

Top plate 312 is opened up by the mechanism driven by the chassis 380 such that the spherical heads 382 of the primary linkages 381 push the top plate 312 upward by physical upward force. This is essentially the expansion mechanism. Contraction or collapsing of the implant 300 involves a different mechanism which is also positioned on the chassis 380. As shown in FIG. 30, a diagonally cut groove 396 in the body of the chassis 385 allows for the diagonal translation of a protrusion 397 in the chassis 380, which is connected to the top plate 312 through connection 398. The contracted implant 300 has the protrusion 397 in its lowermost position on a distal end of the groove 396. This serves to maintain a relatively tight connection and parallel configuration between the top plate 312 and the bottom plate 314. As the expansion mechanism is activated, the protrusion is extended proximally such that it begins to lift up diagonally in the groove 396, thereby lifting the top plate 312. However, if there is desire to contract the implant 300, the protrusion 397 travels back down the groove 396, serving to lower the connection 398 between the top 312 and bottom 314 plates, and therefore the top plate 312 is lowered down toward the bottom plate 314 again. During the expansion process, this sliding protrusion mechanism is passive, and during the contraction mechanism, this sliding protrusion mechanism becomes active to pull down the top plate 312.

Various fixation devices with locking and anti-backout mechanisms may be used with the implants 100, 200, and 300 shown in the present disclosure. One such type is shown in FIGS. 31-33. In this particular embodiment shown, fixation device 444 with anti-backout device has a top circular portion 468 and bottom circular portion 469 having an aperture 467 therein. The middle portion 446 is the engagement mechanism which services to lock into an accommodating portion of an implant, such as those shown in FIGS. 1-2. The device shown contains a canted coil mechanism 449 as its anti-backout mechanism, but other types may also be used to secure the implant position with respect to adjacent vertebra once it is placed and sized.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. An implant device, comprising: a first plate having an extension on an anterior side; a second plate having an extension on an anterior side; a linkage between the first plate and the second plate; and a translation mechanism in the second plate configured to move the linkage from a collapsed configuration wherein the first plate and the second plate are substantially parallel with each other to an expanded configuration wherein the first plate is moved away from the second plate forming an angle between the first plate and the second plate, wherein the extension on the anterior side of the first plate extends toward and over the extension on the anterior side of the second plate and forms at least a portion of an anterior wall of the implant device, and wherein the extension substantially encloses an interior of the implant device in the collapsed configuration.

2. The device of claim 1, wherein the linkage is connected to the second plate via a pin which remains parallel to the plane of the second plate.

3. The device of claim 2, wherein the pin translates within a slot in the second plate.

4. The device of claim 3, wherein when the pin is at a first end of the slot, the first plate is parallel with the second plate.

5. The device of claim 4, wherein when the pin is at a second end of the slot, the first plate forms an angle with the second plate.

6. The device of claim 1, wherein the translation mechanism is activated by a drive shaft positioned within the second plate.

7. The device of claim 1, wherein the first plate and the second plate are connected by a hinge mechanism.

8. An implant device, comprising:
a top plate having an extended anterior wall;
a bottom plate having an extended anterior wall;
a linkage between the top plate and the bottom plate;
wherein a translation mechanism in the bottom plate causes the linkage to move from a collapsed configuration wherein the top plate and the bottom plate are substantially parallel with each other to an expanded configuration wherein the top plate is moved away from the bottom plate forming an angle with respect to the bottom plate,
wherein the extended anterior wall of the top plate extends toward and over the extended anterior wall of the bottom plate, and together the extended anterior wall of the top plate and the extended anterior wall of the bottom plate form an anterior wall of the implant device, and
wherein the extended anterior wall of the top plate and the extended anterior wall of the bottom plate together substantially enclose an interior of the implant device in the collapsed configuration.

9. The device of claim 8, wherein the linkage is connected to the bottom plate via a pin which remains parallel to the plane of the bottom plate.

10. The device of claim 9, wherein the pin translates within a slot in the bottom plate.

11. The device of claim 10, wherein when the pin is at a first end of the slot, the extended anterior wall of the top plate is substantially parallel to the extended anterior wall of the bottom plate.

12. The device of claim 11, wherein when the pin is at a second end of the slot, the extended anterior wall of the top plate forms an angle with the extended anterior wall of the bottom plate.

13. The device of claim 8, wherein the translation mechanism is activated by a moveable chassis positioned within the bottom plate.

* * * * *